(12) United States Patent
Power et al.

(10) Patent No.: US 11,532,392 B2
(45) Date of Patent: Dec. 20, 2022

(54) METER HAVING POST-MEAL TEST-TIME ALARM

(71) Applicant: Ascensia Diabetes Care Holdings AG, Basel (CH)

(72) Inventors: Barry D. Power, Elkhart, IN (US); Jeffrey A. Culver, Sylvania, OH (US)

(73) Assignee: Ascensia Diabetes Care Holdings AG, Basel (CH)

( * ) Notice: Subject to any disclaimer, the term of this patent is extended or adjusted under 35 U.S.C. 154(b) by 36 days.

(21) Appl. No.: 17/131,271

(22) Filed: Dec. 22, 2020

(65) Prior Publication Data

US 2021/0110699 A1 Apr. 15, 2021

Related U.S. Application Data

(63) Continuation of application No. 16/736,735, filed on Jan. 7, 2020, now Pat. No. 10,885,766, which is a continuation of application No. 16/250,761, filed on Jan. 17, 2019, now Pat. No. 10,546,482, which is a continuation of application No. 15/210,307, filed on Jul. 14, 2016, now Pat. No. 10,223,893, which is a continuation of application No. 11/989,815, filed as
(Continued)

(51) Int. Cl.
| | |
|---|---|
| *G16H 40/63* | (2018.01) |
| *A61B 5/145* | (2006.01) |
| *A61B 5/00* | (2006.01) |
| *G08B 21/24* | (2006.01) |
| *G16H 20/10* | (2018.01) |

(52) U.S. Cl.
CPC ......... *G16H 40/63* (2018.01); *A61B 5/14532* (2013.01); *A61B 5/14546* (2013.01); *A61B 5/7475* (2013.01); *G08B 21/24* (2013.01); *G16H 20/10* (2018.01)

(58) Field of Classification Search
None
See application file for complete search history.

(56) References Cited

U.S. PATENT DOCUMENTS

| | | |
|---|---|---|
| 4,686,624 A | 8/1987 | Blum |
| 5,673,691 A | 10/1997 | Abrams |

(Continued)

FOREIGN PATENT DOCUMENTS

| | | |
|---|---|---|
| JP | 2001-221803 | 8/2001 |
| JP | 2003-204941 | 7/2003 |

(Continued)

OTHER PUBLICATIONS

International Search Report and Written Opinion in International Patent Application No. PCT/US2006/030594, dated Nov. 30, 2006 (10 pages).

*Primary Examiner* — Jyoti Nagpaul
(74) *Attorney, Agent, or Firm* — Erise IP, P.A.

(57) ABSTRACT

A method for using a meter and a meter (10) adapted to determine an analyte concentration reading, the meter comprising a display (12) adapted to display information to a user of the meter, the display including information directed to a post-meal test-time alarm (22") that is adapted to remind the user to obtain a post-meal analyte concentration reading, and at least one user input mechanism (15) adapted to allow the user to activate the post-meal test-time alarm.

24 Claims, 1 Drawing Sheet

Related U.S. Application Data application No. PCT/US2006/030594 on Aug. 4, 2006, now abandoned.

(60) Provisional application No. 60/705,957, filed on Aug. 5, 2005.

(56) References Cited

U.S. PATENT DOCUMENTS

| | | | |
|---|---|---|---|
| 5,822,715 A | 10/1998 | Worthington | |
| 6,167,362 A * | 12/2000 | Brown | G09B 19/00 |
| | | | 463/9 |
| 6,246,966 B1 | 6/2001 | Perry | |
| 6,574,425 B1 * | 6/2003 | Weiss | G01N 21/274 |
| | | | 356/402 |
| 6,925,393 B1 | 8/2005 | Kalatz | |
| 7,241,265 B2 | 7/2007 | Cummings | |
| 7,399,277 B2 | 7/2008 | Saidara | |
| 2002/0087054 A1 | 7/2002 | Lin | |
| 2004/0015102 A1 * | 1/2004 | Cummings | G01N 33/48792 |
| | | | 600/584 |
| 2004/0059201 A1 | 3/2004 | Ginsberg | |
| 2005/0038332 A1 | 2/2005 | Saidara | |
| 2005/0038674 A1 | 2/2005 | Braig | |
| 2006/0089540 A1 | 4/2006 | Meissner | |
| 2007/0016170 A1 | 1/2007 | Kovelman | |

FOREIGN PATENT DOCUMENTS

| | | |
|---|---|---|
| TW | 537878 | 6/2003 |
| TW | 592664 | 6/2004 |

\* cited by examiner

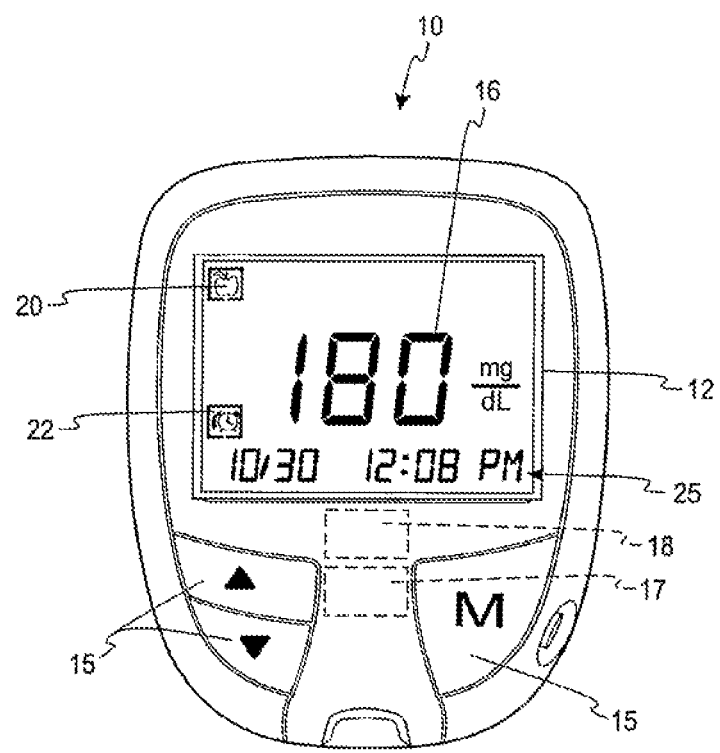

METER HAVING POST-MEAL TEST-TIME ALARM

CROSS-REFERENCE TO RELATED APPLICATIONS

This application is a continuation of U.S. application Ser. No. 16/736,735, filed Jan. 7, 2020, which is a continuation of U.S. application Ser. No. 16/250,761, filed Jan. 17, 2019, now U.S. Pat. No. 10,546,482, which is a continuation of U.S. application Ser. No. 15/210,307, filed Jul. 14, 2006, now U.S. Pat. No. 10,223,893, which is a continuation of U.S. application Ser. No. 11/989,815, filed Jan. 30, 2008, which is a 371 of PCT/US06/30594, filed Aug. 4, 2006, and which claims priority to U.S. Provisional Application No. 60/705,957, filed on Aug. 5, 2005, all of which are hereby incorporated by reference in their entireties.

FIELD OF THE INVENTION

The present invention relates generally to meters and methods of using the same, and more particularly, to a meter having a post-meal test-time alarm for notifying a user when it is time to measure an analyte concentration following a meal.

BACKGROUND OF THE INVENTION

The quantitative determination of analytes in body fluids is of great importance in the diagnoses and maintenance of certain physiological abnormalities. For example, lactate, cholesterol, bilirubin and glucose should be monitored in certain individuals. In particular, determining glucose in body fluids is important to diabetic individuals who must frequently check the glucose concentration in their body fluids to regulate the glucose intake in their diets.

Diabetic individuals often test their blood glucose levels via a blood glucose meter. Health care professionals recognize that it is particularly important for a person with diabetes to test his or her blood glucose level about two hours after a meal. This length of time after a meal represents the time frame when blood glucose levels typically spike and can cause the most harm. Thus, it would be desirable to have a meter that provides a reminder or stimulus to the user to check his or her blood glucose level about two hours after a meal.

SUMMARY OF THE INVENTION

A meter is disclosed according to one embodiment of the present invention. The meter is adapted to determine an analyte concentration reading. The meter includes a display adapted to display information to a user of the meter. The display includes information directed to a post-meal test-time alarm that is adapted to remind the user to obtain a post-meal analyte concentration reading. The meter includes at least one user input mechanism adapted to allow the user to activate the post-meal test-time alarm.

A method for using a meter adapted to determine an analyte concentration reading is disclosed according to one embodiment of the present invention. The meter has a display adapted to display information to a user. The method includes the acts of displaying information relating to a post-meal test-time alarm, activating the post-meal test-time alarm via an input mechanism, and sounding the post-meal test-time alarm after a predetermined amount of time to remind the user to obtain a post-meal analyte concentration reading.

The above summary of the present invention is not intended to represent each embodiment, or every aspect, of the present invention. Additional features and benefits of the present invention are apparent from the detailed description, and FIGURES set forth below.

BRIEF DESCRIPTION OF THE DRAWING

FIG. 1 is a front side view of a meter having a post-meal teat-time alarm feature according to one embodiment of the present invention.

DESCRIPTION OF ILLUSTRATED EMBODIMENTS

The present invention is directed to a meter that is adapted to determine an analyte concentration in a body fluid sample which is collected with a lancing device. Examples of the types of analytes which may be collected include glucose, lipid profiles (e.g., cholesterol, triglycerides, LDL and HDL), microalbumin, hemoglobin A1C, fructose, lactate, or bilirubin. It is contemplated that other analyte concentrations may also be determined. The analytes may be in, for example, a whole blood sample, a blood serum sample, a blood plasma sample, other body fluids like ISF (interstitial fluid) and urine, and non-body fluids. As used within this application, the ten "concentration" refers to an analyte concentration, activity (e.g., enzymes and electrolytes), titers (e.g., antibodies), or any other measure concentration used to measure the desired analyte.

One embodiment of the present invention is a meter 10 as shown in FIG. 1. The meter 10 has a display 12 that is adapted to display information to a user of the meter 10. Some of the information that may be displayed to a user includes concentration readings, time and date indicators, markers and alarms. The meter 10 also has at least one user input mechanism 15 that is adapted to allow the user to make selections relating to one or more user features. The user input mechanism 15 may include, for example, buttons, scroll bars, touch screens, or any combination of such items. The meter 10 may also have a memory device 17 that is adapted to store concentration readings, etc.

According to one embodiment of the present invention, the meter 10 includes a post-meal test-time alarm 18. This alarm 18 is adapted to remind a user to test his or her blood glucose concentration after a meal. Preferably, the alarm 18 reminds a user to test his or her blood glucose concentration about 1½ to about 2½ hours, and most desirably about 2 hours, after a meal. This length of time after a meal has been determined to be the most critical glucose monitoring time since it represents the time frame when blood glucose levels typically spike and can cause the most harm. While some meters provide the capability to program test-time alarms, the present invention automatically ties the alarm to a meal marker and provides for the alarm to go off after a predetermined amount of time. While the remainder of the disclosure herein will be directed towards post-meal test-time alarms associated with glucose meters, it is to be understood that the post-meal test-time alarm may be implemented in meters used for determining other analytes.

Turning in more detail to FIG. 1, the display 12 shows an analyte concentration reading 16. The reading 16 includes the numerical value and the appropriate units, i.e., 180 mg/dL. The display 12 also shows an icon representing a pre-meal marker 20 and an icon representing a post-meal test-time alarm 22. Also included on the display 12 is a time and date indicator 25. Other markers and/or features may be displayed on the display 12 in addition to the items described above.

To illustrate the use of the meter 10 and the post-meal test-time alarm 18 according to one embodiment, once a blood glucose concentration reading 16 is obtained, the meter 10 displays certain markers and/or user features. These features may be pre-programmed into the meter 10 before it is used by a user or the meter 10 may be customized for a particular user's needs after use begins. One of the items displayed is the pre-meal marker icon 20. In the example in FIG. 1, the pre-meal marker icon 20 is represented by the shape of an apple. Upon selection of this icon 20 by a user, the meter 10 automatically responds by flashing the post-meal test-time alarm icon 22. In the example in FIG. 1, the post-meal test-time alarm icon 22 is represented by the face of a clock. The user selects the post-meal test-time alarm icon 22 using the user input mechanism 15 to activate the post-meal test-time alarm 18. In addition to the icons described above, i.e., the apple and the clock, it is contemplated that other icons may be used as indicators of the pre-meal marker and the post-meal test-time alarm.

In some embodiments, the alarm 18 may produce a long beeping sound or shorter successive beeping sounds that occur about 2 to about 3 hours after the pre-meal marker is selected. Ideally, the alarm 18 is sounded about 2½ hours after the pre-meal marker is selected based on the assumption that the pre-meal reading is actually taken ½ hour before the meal so that the insulin has time to start working. Thus, a 2½ hour delay from the selection of the pre-meal marker activates the post-meal test-time alarm 18 which sounds about 2 hours after the user consumes a meal. If the user does not want to activate the post-meal test-time alarm 18, the user may make other selections via the input mechanism 15 and the post-meal test-time alarm icon 22 disappears from the display 12.

In addition to the pre-meal marker described above, others markers may be used to activate an alarm that is associated with certain events. Some examples of other markers (not shown) that may be used with the present invention are exercise markers, medication markers, fasting-time markers, log-book markers, and illness markers. The alarm can also be triggered after specific events such as a low or high concentration reading. For example, in one embodiment, an alarm can be triggered one hour after a low concentration reading. In another embodiment, the alarm can be triggered two hours after a high concentration reading. Additionally, the user can set an alarm to be triggered at a specific time each day, such as a noon-time alarm. While the use of the alarm is not tied to a specific event in that case, it reminds the user to take a concentration reading at a particular time each day.

Some commercially available meters, such as those that are manufactured and/or sold by Bayer Healthcare LLC of Tarrytown, N.Y., may be redesigned to incorporate the present invention, such as the Ascensia® CONTOUR® Blood Glucose Monitoring System and the Ascensia® BREEZE® Blood Glucose Monitoring System. It is contemplated that other meters, in addition to the ones listed above, may incorporate the present invention as described herein.

Alternative Embodiment A

A meter adapted to determine an analyte concentration reading, the meter comprising a display adapted to display information to a user of the meter, the display including information directed to a post-meal test-time alarm that is adapted to remind the user to obtain a post-meal analyte concentration reading, and at least one user input mechanism adapted to allow the user to activate the post-meal test-time alarm.

Alternative Embodiment B

The meter according to Alternative Embodiment A, further comprising a memory device adapted to store the analyte concentration reading.

Alternative Embodiment C

The meter according to Alternative Embodiment A, wherein the analyte is glucose.

Alternative Embodiment D

The meter according to Alternative Embodiment A, wherein the post-meal test-time alarm is adapted to remind the user to obtain the post-meal analyte concentration reading after a predetermined amount of time.

Alternative Embodiment E

The meter according to Alternative Embodiment D, wherein the post-meal test-time alarm is adapted to remind the user to obtain the post-meal analyte concentration reading about 1½ to about 2½ hours after a meal.

Alternative Embodiment F

The meter according to Alternative Embodiment B, wherein the post-meal test-time alarm is adapted to remind the user to obtain the post-meal analyte concentration reading about 2 hours after a meal.

Alternative Embodiment G

A method for using a meter adapted to determine an analyte concentration reading, the meter having a display adapted to display information to a user, the method comprising the acts of displaying information relating to a post-meal test-time alarm, activating the post-meal test-time alarm via an input mechanism, and sounding the post-meal test-time alarm after a predetermined amount of time to remind the user to obtain a post-meal analyte concentration reading.

Alternative Process H

The method according to Alternative Process G, further comprising storing the post-meal analyte concentration reading.

Alternative Process I

The method according to Alternative Process G, wherein the analyte is glucose.

Alternative Process J

The method according to Alternative Process G, wherein the sounding of the post-meal test-time alarm occurs about 1½ to about 2½ hours after a meal.

Alternative Process K

The method according to Alternative Process J, wherein the sounding of the post-meal test-time alarm occurs about two hours after a meal.

While the invention is susceptible to various modifications and alternative forms, specific embodiments and methods thereof have been shown by way of example in the drawing and are described in detail herein. Specifically, it is contemplated that many other markers may be used with the present invention to activate alarms in the same manner as described herein. It should be understood, however, that the description herein is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A method for displaying information to a user, the method comprising:
    providing a device including a display and a memory,
    wherein the display is configured to display an analyte concentration reading and an icon representing a pre-event marker;
    in response to receiving a selection of the icon representing the pre-event marker:
        marking the analyte concentration reading as a pre-event analyte concentration reading associated with an event; and
        displaying an icon representing a post-event test-time alarm on the display; and
    in response to determining that the post-event test-time alarm is activated, automatically triggering the post-event test-time alarm at a predetermined time,
    wherein the post-event test-time alarm is configured to remind the user to obtain a post-event analyte concentration reading,
    wherein the predetermined time is based on the event associated with the pre-event analyte concentration reading.

2. The method of claim 1, further comprising storing the post-event analyte concentration reading in the memory.

3. The method of claim 1, wherein the analyte is glucose.

4. The method of claim 1, wherein the event is a meal.

5. The method of claim 4, wherein the predetermined time is about 1½ to about 2½ hours from the displaying of the analyte concentration reading on the display.

6. The method of claim 4, wherein the triggering of the post-event test-time alarm occurs about two hours after a meal.

7. The method of claim 1, wherein the event is exercise, medication, fasting, illness, or a combination thereof.

8. The method of claim 1, further comprising receiving, via a user input mechanism, a selection of the icon representing a pre-event marker to mark the analyte concentration as a pre-event analyte concentration.

9. The method of claim 1, wherein the device is a meter.

10. The method of claim 1, further comprising displaying the icon representing a pre-event marker on the display.

11. A method for displaying information to a user, the method comprising:
    providing a device including a display and a memory,
    wherein the display is configured to display an analyte concentration reading;
    in response to receiving a selection of an icon representing a pre-event marker, marking the analyte concentration reading as a pre-event analyte concentration reading,
    wherein the pre-event analyte concentration reading is associated with an event;
    in response to marking the pre-event analyte concentration reading, displaying an icon representing a post-event test-time alarm on the display; and
    in response to determining that the post-event test-time alarm is activated, triggering the post-event test-time alarm at a predetermined time,
    wherein the post-event test-time alarm is configured to remind the user to obtain a post-event analyte concentration reading, and
    wherein the predetermined time is based on the event associated with the pre-event analyte concentration reading.

12. The method of claim 11, further comprising storing the pre-event analyte concentration reading and the post-event analyte concentration reading in the memory.

13. The method of claim 11, wherein the analyte is glucose.

14. The method of claim 11, wherein the event is a meal.

15. The method of claim 14, wherein the predetermined time is about 1½ to about 2½ hours from the displaying of the analyte concentration reading on the display.

16. The method of claim 14, wherein the triggering the post-event test-time alarm occurs about two hours after a meal.

17. The method of claim 11, wherein the device is a meter.

18. The method of claim 11, further comprising displaying the icon representing a pre-event marker on the display.

19. A method for displaying information to a user, the method comprising:
    providing a device including a display, at least one processor, and one or more non-transitory computer-readable memory storing computer-executable instructions that, when executed by the at least one processor, carry out actions comprising:
        displaying, on the display, an analyte concentration reading;
        providing, via the device, a first indication representing a pre-event marker;
        receiving a selection, by a user, of the first indication representing the pre-event marker;
        in response to receiving the selection:
            marking the analyte concentration reading displayed on the display as a pre-event analyte concentration reading associated with an event; and
            automatically triggering a post-event test-time alarm at a predetermined time,
            wherein the predetermined time is based on an event associated with the pre-event analyte concentration reading, and
            wherein the post-event test-time alarm is configured to remind the user to obtain a post-event analyte concentration reading.

20. The method of claim 19, wherein the event associated with the pre-event analyte concentration reading is one of an exercise event, a medication event, a fasting event, or an illness event.

21. The method of claim 19,
    wherein the event is a measured analyte concentration reading above a threshold analyte concentration value, and
    wherein the predetermined time is about two hours.

22. The method of claim 19,
wherein the event is a measured analyte concentration reading below a threshold analyte concentration value, and
wherein the predetermined time is about one hour.

23. The method of claim 19,
wherein the selection is a first selection, and
wherein the actions further comprise:
responsive to receiving a second selection, deactivating the post-event test-time alarm.

24. The method of claim 19, wherein the selection is received via a user input mechanism, the user input mechanism comprising at least one of a button, a touch screen, or a scroll bar.

\* \* \* \* \*